United States Patent [19]

Schmid et al.

[11] 4,294,745

[45] Oct. 13, 1981

[54] CURABLE MIXTURE FOR PRODUCING REINFORCED ELASTOMERIC PLASTICS BASED ON EPOXIDE RESIN

[75] Inventors: Rolf Schmid, Gelterkinden; Friedrich Lohse, Oberwill, both of Switzerland

[73] Assignee: Ciba-Geigy Corporation, Ardsley, N.Y.

[21] Appl. No.: 109,739

[22] Filed: Jan. 4, 1980

[30] Foreign Application Priority Data

Jan. 16, 1979 [CH] Switzerland .................. 403/79
Jan. 16, 1979 [CH] Switzerland .................. 404/79

[51] Int. Cl.$^3$ ............................................. C08L 63/00
[52] U.S. Cl. ............................................. 260/37 EP
[58] Field of Search .................................... 260/37 EP

[56] References Cited

U.S. PATENT DOCUMENTS

| | | | |
|---|---|---|---|
| 3,337,509 | 8/1967 | Budnowski et al. | 260/37 EP |
| 3,483,168 | 12/1969 | Forster et al. | 260/37 EP |
| 3,496,122 | 2/1970 | Niklaus et al. | 260/37 EP |
| 3,506,735 | 4/1970 | Aggias | 260/37 EP |
| 3,629,184 | 12/1971 | Kawam et al. | 260/37 EP |
| 3,668,177 | 6/1972 | Van Herpt | 260/37 EP |
| 4,009,043 | 2/1977 | Preis | 260/37 EP |

OTHER PUBLICATIONS

C. A., 54, 9156c (1960); *Fibrous Alumina Monohydrate.*

*Primary Examiner*—Lewis T. Jacobs
*Attorney, Agent, or Firm*—Luther A. R. Hall

[57] ABSTRACT

The mixture contains as reinforcing agent needle-shaped crystals insoluble in epoxide resin, the crystals being for example of aluminium oxide or hydroxide and acetic acid, propionic acid, benzoic acid, adipic acid or sebacic acid. These crystals improve specific mechanical properties of the elastomeric polymers obtained by curing the epoxide resin/curing agent mixture, without the elastomeric properties being lost.

11 Claims, No Drawings

CURABLE MIXTURE FOR PRODUCING REINFORCED ELASTOMERIC PLASTICS BASED ON EPOXIDE RESIN

The invention relates to a curable mixture for producing reinforced elastomeric plastics based on epoxide resin, which mixture contains, as reinforcing agents, needle-shaped crystals which are insoluble in epoxide resin and which have a specific density and dimensions.

The method of reinforcing epoxide resins with fibrous fillers, such as carbon or glass fibres, is known. In the case of longer-chain epoxide resins, which can be converted into elastomeric moulded materials, there is obtained with glass fibres an increase in strength values but the high elongation at break, by virtue of which moulded materials made from elastomeric epoxide resins are characterised, is lost when glass fibres are used for reinforcement.

The production of needle-shaped aluminium oxide monohydrate and the use thereof for improving the mechanical properties of elastomeric plastics by incorporating an amount of 1-30 percent by weight into the plastics material are known from the U.S. Pat. No. 2,915,475. Tests made by us have however shown that the aluminium oxide monohydrate known from the said U.S. patent specification is not suitable for reinforcing elastomeric epoxide resins.

It has now been found that needle-shaped crystals which are insoluble in epoxide resin and which have a specific density and dimensions constitute excellent reinforcement fillers for elastomeric epoxide resins, since the elastomeric epoxide resins reinforced in this manner produce moulded materials which are distinguished both by high strength and by increased toughness and elasticity.

The invention thus relates to a curable mixture containing (1) an epoxide resin, and
(2) a curing agent for epoxide resins, wherein (a) at least one of the components (1) and (2) is at least trivalent, (b) the components (1) and (2) together consist to the extent of at least 60 percent by weight, preferably at least 90 percent by weight, of aliphatic chain segments, (c) the number of atoms in the chains of components (1) and (2) between two active groups is 25 to 700, preferably 80 to 350, a phenylene group being reckoned to have 4 atoms, and (d) the components (1) and/or (2) contain aliphatic chain segments in the form of polyester or polyether groups, or hydrocarbon radicals unsubstituted or substituted in the side chain; the curable mixture also containing (3) an amount of 1 to 20 percent by weight, preferably 5 to 12 percent by weight, relative to the total amount of components (1) to (2), of needle-shaped to rod-shaped crystals which are insoluble in epoxide resin, and which have a length of 0.1 to 600 μm, preferably 4 to 200 μm, a thickness of 0.01 to 60 μm, preferably 0.2 to 10 μm, a length/thickness ratio of 3 to 200, preferably 5 to 50, and a density of 1.3 to 3.0, preferably 1.3 to 1.7.

The curable mixture contains as component (3) in particular anhydrous, needle-shaped aluminium monohydroxycarboxylic acid salts which are obtained by reaction of neutral or basic aluminium oxide or aluminium hydroxide with acetic acid, propionic acid, benzoic acid, a dicarboxylic acid of the formula $HO_2C-C_nH_{2n}-CO_2H$, wherein n is a number from 3 to 10 inclusive, and the group $-C_nH_{2n}-$ is preferably a linear alkylene group, or with the anhydrides of carboxylic acids, which salts are 0.1 to 200 μm long and 0.01 of 10 μm thick, and have a length/thickness ratio of 5:1 to 50:1, preferably 10:1 to 20:1.

The curable mixture contains as component (1) preferably a compound having 3 epoxide groups, such as triglycidylisocyanurate or 1,3-bis-(1-glydicyl-5,5-dimethyl-hydantoin-3-yl)-2-glycidyloxy-propane; and the mixture contains as component (2) preferably an aliphatic, noncrystalline polycarboxylic acid having a molecular weight of 1500 to 6000, preferably 3000 to 4500, especially a linear acid polyester or polyether having terminal carboxyl groups, such as an acid adipic acid-neopentyl glycol polyester, or an acid polyester formed from polymethylene glycol and a dimerised fatty acid.

The curable mixture can also advantageously contain, as component (1), a linear polyether or polyester having terminal glycidyl groups bound ether-like or ester-like, the molecular weight being between 1500 and 6000; and, as component (2), a polyamine having at least 3 amino hydrogen atoms active during the curing process, with the proviso that the above-mentioned conditions under (b), (c) and (d) are likewise satisfied.

The following are given as examples of component (1):

(A): 3250 g of an acid polyester formed from sebacic acid and neopentyl glycol (molar ratio for the production of the polyester: 11:10), with an acid equivalent weight of 1080, and 1750 g of triglycidylisocyanurate having an epoxide content of 9.1 epoxide equivalents/kg are allowed to react for 3 hours at 140° C. The adduct obtained is a brown viscous substance having an epoxide equivalent weight of 373.

(B): 3000 g of an acid polyester from adipic acid+neopentyl glycol (molar ratio: 8:7), with an acid equivalent weight of 705, and 1500 g of tetrahydrophthalic acid diglycidyl ester having an epoxide content of 6.4 epoxide equivalents/kg are allowed to react for 3 hours at 140° C. The adduct obtained is a light-brown viscous substance having an epoxide equivalent weight of 1062.

(C): 2000 g of an acid polyester from adipic acid+neopentyl glycol (molar ratio: 8:7), with an acid equivalent weight of 705, and 1000 g of diphenylolpropane diglycidyl ether having an epoxide content of 5.4 epoxide equivalents/kg are allowed to react for 3 hours at 140° C. The adduct obtained is a light-brown viscous substance having an epoxide equivalent weight of 1290.

Further suitable curable mixtures are for example those which contain, as component (1), an epoxide compound having 3 epoxide groups, such as triglycidylisocyanurate, and, as component (2), a polyester polycarboxylic acid with segments of the formula I $$-O-R_1-O-CO-R_2-CO-_q \qquad (I)$$

in which $R_1$ and $R_2$ independently of one another are each an alkylene group having at least 2 C atoms in the chain, and per O bridge on average at least 3.5 and at most 30 C atoms, not taking into account the C atoms of the $-CO-O-$ groups, are present in the chain, and wherein the radicals $R_1$ and $R_2$ together contain at least one alkyl group, one cycloalkyl group or an aryl group as substituents for an H atom, and in which q is a number from 2 to 40 inclusive, which however is sufficiently large for the segment to contain in the chain at least 30

C atoms, not taking into account the C atoms of the —CO—O— groups. To 1 equivalent of epoxide compound there are preferably 0.7 to 1.2, particularly 0.9 to 1.1, equivalents of polyester carboxylic acid. Suitable polyester carboxylic acids are for example those based on the following polyalcohols and polycarboxylic acids:

11 mols of sebacic acid—10 mols of neopentyl glycol
8 mols of adipic acid—7 mols of neopentyl glycol
13 mols of adipic acid—12 mols of neopentyl glycol
8 mols of adipic acid—7 mols of trimethylhexanediol
8 mols of trimethyladipic acid—7 mols of neopentyl glycol
21 mols of adipic acid—20 mols of neopentyl glycol
4 mols of dimerised fatty acid—3 mols of diethylene glycol 3 mols of dimerised fatty acid—2 mols of hexanediol
glycerol-adipic acid-butanediol-neopentyl (1:9:3:3)
trimethylhexanediol-adipic acid-hexanediol-neopentyl glycol (1:8:2:3).

In the formula I, $R_2$ can also be a group derived from a dimerised singly or doubly unsaturated fatty acid.

Examples of such polyester polycarboxylic acids are derived from the following polyalcohols and polycarboxylic acids:

4 mols of dimerised fatty acid—3 mols of diethylene glycol
4 mols of dimerised fatty acid—3 mols of hexanediol
3 mols of dimerised fatty acid—2 mols of hexanediol.

Details concerning the fundamental aspects of the production of long-chain, aliphatic polyester polycarboxylic acids of the said type are to be gathered from a publication of H. Batzer et al. in "Die Angewandte Makromoleculare Chemie" (Applied Macromolecular Chemistry) 1973, pp. 349–411.

The needle-shaped crystals contained as component (3) in the curable mixtures can be inorganic compounds, such as anhydrous calcium sulfate obtainable commercially, or inorganic-organic compounds, for example the aluminium monohydroxycarboxylic acid salts free from water of crystallisation.

The production of these aluminium salts, which has hitherto not been described in the literature, can be carried out in known commercial equipment by a process comprising reacting neutral or basic aluminium oxide or aluminium hydroxide, in the presence of an inert solvent or without solvent, with the exclusion of water and at elevated temperatures, with acetic acid, propionic acid or benzoic acid, or with a dicarboxylic acid of the formula $HO_2C-C_n-CO_2H$, wherein n is a number from 3 to 10 inclusive, or acid anhydrides thereof, or with mixtures of these carboxylic acids or anhydrides, and continuously removing the reaction water from the reaction mixture.

Suitable aluminium oxides and hydroxides are for example: $Al_2O_3$, $Al(OH)_3$, $AlO(OH)$, $Al_2O_3.H_2O$ and $Al_2O_3.3H_2O$. Freshly precipitated aluminium hydroxide is preferably used. The filler to be used according to the invention and optionally further additives can be incorporated into the curable elastomeric epoxide resin mixture by mixing them in by methods customary in industry. The curable epoxide resin mixtures filled with the needle-shaped crystals are further characterised by favourable processing characteristics, and can be cast like normal casting resins since there occurs as a result of the filler only a relatively small increase in viscosity. By virtue of the low specific weight of the filler to be used according to the invention, no sedimentation, or only a slight sedimentation, takes place in the casting resins, so that also moulded materials produced from these casting resins display a uniform distribution of the filler. Even with small additions, there is obtained with the fillers to be used according to the invention an extraordinary reinforcing effect. The moulded materials produced from the curable mixtures according to the invention have improved mechanical properties with regard to tensile strength, tear propagation resistance, notch impact strength, toughness and elongation. The stated improvements occur without the needle-shaped fillers having been orientated in a specific direction before curing of the curable mixture.

PRODUCTION OF NEEDLE-SHAPED CRYSTALLINE ALUMINIUM COMPOUNDS

Example I

Two liters of o-dichlorobenzene are placed into a 6-liter sulfonating flask, provided with stirrer, thermometer, and distillation head with descending condenser, and 1168 g (8 mols) of adipic acid is suspended therein. The mixture is then heated with stirring until, at an internal temperature of 150°–155° C., a homogeneous solution has formed, whereupon 312 g (4 mols) of aluminium hydroxide, $Al(OH)_3$, is added. The temperature in the reaction mixture is now further raised until at 170° C. aqueous o-dichlorobenzene commences to distill off. The advancement of the reaction is manifested by a constant increase of suspended substance and by the fact that stirring becomes more difficult. During the entire duration of reaction of 96 hours, 2100 ml of aqueous o-dichlorobenzene is distilled off. This amount is replaced by the continuous addition of 4200 ml of o-dichlorobenzene. As the reaction proceeds, it is possible under the microscope to observe the increasing appearance of the needle-shaped product. In further processing, the hot reaction mixture is filtered under suction, and the filter residue is stirred up four times with 6 liters of isopropanol at 75° C., and subsequently filtered off. The product purified in this manner is dried for 48 hours at 100° C./2 kPa to thus yield 723 g of a colourless needle-shaped product; elementary analysis: C 37.46%, H 5.11% and Al 14.10%. The length of the needles varies between 0.1–4.0 μm and the width between 0.05–0.15 μm; the density was determined as being 1.40 g/cm$^3$, and the spec. surface area as being 2.81 m$^2$/g (using the method of nitrogen adsorption of Brunauer, Emmett and Teller). The product commences to decompose at 410° C. (thermogravimetrical analysis TGA, in air).

Example II

To 100 ml of dimethylformamide is added 438 g (3 mols) of adipic acid. The pastry mixture is heated to 130° C., whereupon a homogeneous solution is formed. To this is then added 51 g (0.5 mol) of aluminium oxide (activity stage I, basic, JCN Pharmaceuticals GmbH, Eschwege, Germany). The mixture is further heated until a slight refluxing occurs. The reaction mixture rapidly becomes viscous, so that after 4 hours reaction time a further 550 ml of dimethylformamide has to be added in order to keep the mixture readily stirrable. The reaction is then continued for 43 hours with slight refluxing. The mixture is subsequently filtered hot; the filter residue is stirred up four times with 1.5 liters of isopropanol each time, filtered, and finally dried at 100°

C./13.3 Pa until constant weight is attained. The yield is 168.6 g of a colourless, needle-shaped product.

Elementary analysis: C 35.70%; H 4.68%; Al 15.90%.

Example III

In a 1.5-liter sulfonating flask, fitted with stirrer, thermometer, and distillation head with descending condenser, 39 g (0.5 mol) of aluminium hydroxide (hydrargillit) and 230 g (1.0 mol) of pure sebacic acid (Fluka) are suspended in 400 ml of o-dichlorobenzene by heating at 177° C. At this internal temperature, the aqueous o-dichlorobenzene slowly commences to distill of azeotropically, and after 20 hours reaction time the suspension becomes viscous. The mixture is maintained readily stirrable by constant replacement of the distillate (600 ml) and addition of fresh o-dichlorobenzene (total 850 ml). The hot suspension is filtered after 80 hours' reaction time; the residue is washed four times with 1 liter of isopropanol at 70° C. each time, filtered, and subsequently dried at 110° C./13.3 Pa. The yield is 73.4 g of a fine, needle-shaped product.

Elementary analysis: C 35.50%, H 6.50%; Al 16.70%; density: 1.42 g/cm$^3$; spec. surface area: 22.5 m$^2$/g.

Example IV

In a 4.5-liter sulfonating flask, fitted with stirrer, thermometer, and distillation head with descending condenser, 273 g (3.5 mols) of finely powdered aluminium hydroxide (a product obtainable from Merck under the tradename of "Hydrargillit") is added, with stirring, to 2100 g (35 mols) of acetic acid, and the mixture is heated, whereupon at 114° C. internal temperature (130° C. bath temperature) a slow distilling off of aqueous acetic acid commences. In order to maintain stirrability and to replace the acetic acid distilled off, there is added, in the course of the total reaction time of 72 hours, in all a further 1000 ml of fresh acetic acid in 100 ml portions. The progress of the reaction can easily be followed under the microscope, and the insoluble product at the end of the process is in the form of fine needles. It is filtered off hot, stirred up four times with 2000 ml of isopropanol at 70° C. each time, and filtered, and subsequently dried at 100° C./13.3 Pa. The yield is 553 g of fine colourless, needle-shaped product.

Elementary analysis: found: C: 29.10%; H: 4.20%; Al: 16.35% calculated: C: 29.63%; H: 4.36%; Al: 16.61%.

It can be concluded from the composition and IR spectra that the structural formula is as follows:

HO—Al—(OCOCH$_3$)$_2$;C$_4$H$_7$O$_5$Al

Example V

Into a 1-liter steel autoclave with stirrer are placed 39.0 g (0.5 mol) of aluminium hydroxide ("Hydrargillit"), 244 g (2.0 mols) of benzoic acid and 500 ml of water. The mixture is heated for 12 hours at 170° C./15 bars. After cooling, the reaction product is filtered off, and the filter residue is heated four times with 1.5 liters of isopropanol at 70° C. each time, and then filtered. After drying in a vacuum chamber at 100° C./10.4 kPa, the yield is 134.1 g (93.7%) of crystalline (needles, 0.15–2 μm long and 0.05–0.25 μm wide) aluminium hydroxydibenzoate: density: 1.41±0.03 g/cm$^3$; spec. surface area: 60.4±1.2 m$^2$/g. C$_{14}$H$_{11}$O$_5$Al (286.219).

Found: C: 57.84; H: 3.915; Al: 9.47%; calculated: C: 58.74; H: 3.87; Al: 9.43%.

The IR spectra agree with the given formula.

IR (KBr): 3700(OH), 3060, 3020 (CH=CH), 1610, 1570, 1500, 1430 (aryl) cm$^{-1}$.

EXAMPLES

Example 1

(a) 65.4 g of a polypropylene glycol diglycidyl ether (=0.2 equiv.) is heated to 40° C. and well mixed with 7.7 g (=0.2 equiv.) of trimethylhexamethylenediamine and, after exhaustion in vacuo, the mixture is poured into aluminium moulds having dimensions of 150×150×1 mm. There are obtained after a heat treatment for 8 hours at 100° C. elastic moulded plates, from which are stamped out specimens corresponding to VSM 77101 (test specimen No. 1) (corresponding to ISO 527). The following properties are determined:

| | |
|---|---|
| tensile strength (TS) | = 0.4 N/mm$^2$ |
| elongation at break (EB) | = 10% |
| toughness (To) $\left[\dfrac{TS \cdot EB}{2}\right]$ | = 2 N/mm$^2$ |
| tear propagation resistance (TPR)* | = 0.93 N/mm |

*measured as load at which further tearing of the identical notched specimen occurs (b) When 6 percent by weight of Al. sebacate needles according to Example III is incorporated, with the aid of a three-roller mill, into the mixture described under (a), the procedure otherwise being as under (a), specimens having the following properties are obtained:

TS=1.3 N/mm$^2$

EB=18%

To=12 N/mm$^2$

TPR=3.2 N/mm

The toughness of the rubber can be increased sixfold by the addition of 6 percent by weight of needles.

Example 2

74 g (=0.1 equiv.) of an adduct, produced by four hours' stirring of 2.5 equiv. of diglycidyl dimethylhydantoin and 687 g (=1.0 equiv.) of an acid adipic acidneopentyl glycol polyester at 140° C. in an N$_2$ atmosphere, is heated at 120° C. and mixed with 15.4 g (=0.1 equiv.) of hexahydrophthalic anhydride and 0.18 g of 1-methylimidazole: mixture A.

The following additives are in the respective cases mixed into a portion of the mixture A:

mixture B: 6 percent by weight of the reaction product aluminium oxide-sebacic acid according to Example III.

mixture C: 6 percent by weight of the reaction product aluminium oxide-adipic acid according to Example I.

After exhaustion in vacuo, the mixtures are poured into aluminum moulds. Curing for 16 hours at 140° C. yields tough moulded specimens having following properties:

| | A | B | C | |
|---|---|---|---|---|
| TS | 6.9 | 9.6 | 12 | N/mm$^2$ |
| EL | 141 | 107 | 121 | % |
| To | 4.9 | 5.1 | 7.3 | N/mm$^2$ |
| TPR | 10.5 | 21 | 20 | N/mm |

The most remarkable aspect in the case of this tough plastics material is the great improvement of the TPR.

Example 3

68.7 (=0.1 equiv.) of an acid adipic acid-neopentylglycol polyester is heated at 110° C. and well mixed with 16.7 g (=0.1 equiv.) of a triepoxide of the following formula

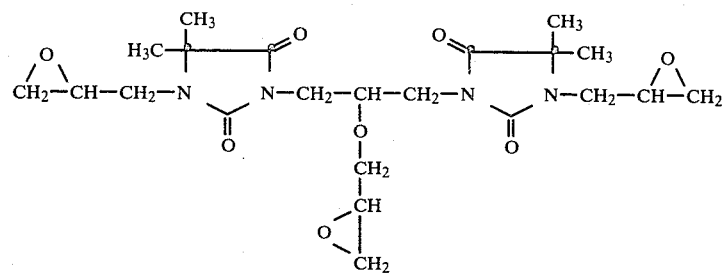

and 0.18 g of 1-methylimidazole: mixture A. Into portions of this mixture are mixed glass fibres (mixture B), or various amounts of a needle-shaped additive (mixtures C, D and E). After exhaustion in vacuo, the mixtures are poured into the 1 mm thick aluminium moulds. Curing for 16 hours at 140° C. yields moulded specimens having the following properties:

|  | A | B | C | D | E |  |
|---|---|---|---|---|---|---|
| TS | 1.45 | 2.3 | 2.8 | 4.7 | 6.8 | N/mm² |
| EL | 119 | 111 | 158 | 163 | 182 | % |
| To | 0.96 | 1.3 | 2.2 | 3.8 | 6.2 | N/mm² |
| TPR | 3.1 | 5.5 | 4.5 | 10.3 | 14.1 | N/mm |
| modulus of elasticity | 1.3 | 3.8 | 2.8 | 7.1 | — |  |

A = without additive
B = addition of 7% of glass fibres + 2% of "Aerosil" *
C = addition of 2% of the reaction product of aluminium oxide and adipic acid according to Example II;
D = addition of 7% of the reaction product of aluminium oxide and adipic acid according to Example II; and
E = addition of 10% of the reaction product of aluminium oxide and adipic acid according to Example II.
* With the addition of glass fibres, it is necessary to add an amount of a thixotropic agent since otherwise severe sedimentation occurs during processing.

Example 4

(a) 68.7 g (=0.1%) of an adipic acid neopentyl glycol polyester is heated at 130° C. and mixed with 10.7 g (0.1 equiv.) of triglycidyl isocyanurate (TGIC). After the TGIC has dissolved, the mixture is cooled to 110° C. and mixed with 0.18 g of 1-methylimidazole; mixture A. Into a portion of this mixture is mixed 6 percent by weight, relative to the resin/curing agent mixture, of the reaction product of aluminium hydroxide and adipic acid according to Example 1. Curing of the mixtures for 16 hours at 130° C. yields moulded specimens having a rubbery-elastic behaviour and the following properties:

|  | A | B |  |
|---|---|---|---|
| TS | 1.5 | 5.0 | N/mm² |
| EL | 150 | 139 | % |
| To | 1.1 | 3.5 | N/mm² |
| TPR | 2.6 | 7.7 | N/mm |

(b) With use of a polyester of identical structure but having an equivalent weight of 1990, the following values are measured:

|  | A | B |  |
|---|---|---|---|
| TS | 3.0 | 12 | N/mm² |
| EL | 700 | 700 | % |
| To | 11 | 42 | N/mm² |
| TPR | 2.2 | 8.8 | N/mm |

A: without addition of a needle-shaped aluminium compound;
B: with addition of 6% of a reaction product of aluminium oxide and adipic acid according to Example II.

EXAMPLE 5

An acid polyester from 23 mols of adipic acid and 22 mols of neopentyl glycol is produced using the melt process. The polyester obtained has an acid equivalent weight of 1532. An amount of 9 g (about 6 percent by weight) of aluminium adipate needles, produced according to Example II, is incorporated, with the aid of a three-roller mill, into 153 g (=0.1 equiv.) of the polyester described above; the material is heated to 130° C., and then well mixed with 11.0 g (=0.1 equiv.) of triglycidyl isocyanurate. The temperature is lowered to 100° C., and 0.3 g of an accelerator of the following structure

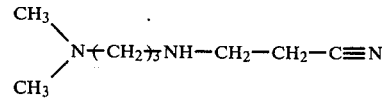

is added, and the whole is thoroughly stirred. The mixture is processed in a manner corresponding to that of Example 3 to obtain moulded specimens having the following properties.

TS=10.0 N/mm² (2.4)

EL=760% (368).

The values in brackets are obtained from the corresponding moulded specimens without aluminium adipate needles.

The high elongation at break of the elastomeric epoxide resins is still further improved by the addition of the needles. The tensile strength is increased even fourfold.

Example 6

An acid polyester is produced from a mixture of 21 mols of adipic acid and 20 mols of neopentyl glycol using the melt process. The polyester obtained has an acid equivalent weight of 1461. An amount of 9.4 g of aluminium acetate needles, produced according to Example IV, is incorporated, with the aid of a three-roller mill, into 146 g (=0.1 equiv.) of the polyester described above, and the material is subsequently heated to 130° C. There is then added to the mixture, with stirring, 11 g (=0.1 equiv.) of triglycidyl isocyanurate (TGIC), and after about 5 minutes the TGIC has been dissolved. The mixture is somewhat cooled and subsequently mixed with 0.3 g of the accelerator used in Example 5. The mixture is poured into 2 mm thick moulds (2×150×150 mm), and cured for 14 hours at 140° C. The specimens, which are stamped out according to ISO 527, have the following properties:

tensile strength: 7.8 (2.6) N/mm$^2$
elongation at break: 529 (339) %.

The values given in brackets are measured on the analogous specimens without reinforcing agent. With regard both to strength and to elongation, there is achieved a surprisingly large increase of these values by the addition of only 6% of needles.

Example 7

The procedure is carried out according to Example 6 with the only exception that, in the place of the aluminium acetate needles, needles based on benzoic acid according to Production Example V are incorporated into the polyester. The specimens obtained after curing have the following properties:

tensile strength: 11.7 N/mm$^2$
elongation at break: 548%.

Example 8

An acid polyester is produced starting with 8 mols of adipic acid and 7 mols of neopentyl glycol and using the melt process. 68.7 g (=0.1 equiv.) of the polyester obtained is ground with 5 g of aluminium acetate needles, obtained according to Production Example IV, on a three-roller mill, and cured, as in Example 6 with 0.1 equiv. of triglycidyl isocyanurate. The specimens produced therefrom have the following properties:

tensile strength:=4.3 (1.5) N/mm$^2$
elongation at break=255 (148) %
tear propagation resistance=4.8 (2.6) N/mm.

(In brackets are again given the values measured on the analogous specimens without addition of the reinforcing agent.)

This Example illustrates the enormous improvement in strength and tear propagation resistance of the notched tensile specimen by the addition of 6% of needles, without the elongation at break being reduced.

Example 9

An acid polyester is produced from 23 mols of adipic acid and 22 mols of nepoentyl glycol using the melt process. The polyester obtained has an acid equivalent weight of 1532. An amount of 9 g (6 percent by weight) of the aluminium acetate needles produced according to Example IV is incorporated, with the aid of a three-roller mill, into 153 g (0.1 equiv.) of the polyester described above; the material is heated to 130° C., and then well mixed with 11.0 g (0.1 equiv.) of triglycidyl isocyanurate. After the addition of 0.3 g of the accelerator described in Example 5, the mixture is cast into the moulds, and cured according to Example 1. There are obtained rubbery-elastic moulded specimens, from which there are stamped out, according to ISO 527, test specimens which have the following properties:

tensile strength=12.5 N/mm$^2$ (2.4)
elongation at break=578% (368).

The values given in brackets are obtained on the analogous test specimens without the reinforcing agent. A comparison shows that the test specimens reinforced according to the invention have an eightfold better toughness value. The employed aluminium acetate needles have the following dimensions:

length: 0.3 to 1.9 $\mu$m
thickness: 0.02 to 0.5 $\mu$m
length/thickness=9 (mean value).

Comparative Example

Aluminium monohydrate is produced according to the instruction given in Example 33 of the U.S. Pat. No. 2,915,475. The fine pulverulent material has the following dimensions: length as thickness=40 to 400 $\mu$m. The aluminium monohydrate is correspondingly incorporated in the same amount into the polyester produced according to Example 9, and then mixed with triglycidyl isocyanurate and the accelerator used in Example 9, so that the amount of the said filler is likewise 6 percent by weight. Already during processing, the aluminium monohydrate exhibited a severe sedimentation, which does not occur with the needles to be used according to the invention. The test specimens produced analogously give only low strength values:

tensile strength=0.85 N/mm$^2$
elongation at break=132%.

The aluminium monohydrate produced by the known process is hence not suitable for reinforcing elastomeric epoxide resins.

Example 10

Example 9 is repeated except that there is incorporated, in place of the aluminium acetate needles used therein, 6 percent by weight of anhydrous calcium sulfate needles (obtainable commercially under the trade name "Anhydridfaser 231B"). The moulded materials cured according to Example 1 have the following properties:

tensile strength=5.2 N/mm$^2$
elongation at break=870%.

The CaSO$_4$ needles used above had the following dimensions:

length=1 to 10 $\mu$m
thickness=50 to 600 $\mu$m
length/thickness=50.

Comparison

Example 10 is repeated except that in place of the CaSO$_4$ needles used therein, 6 percent by weight of gypsum fibres (trade name "SKW 230 A") having the following dimensions:

length=20 to 500 $\mu$m
thickness=10 to 200 $\mu$m
length/thickness=2 is incorporated into the elastomeric epoxide resin mixture.

The moulded materials cured according to Example 1 have the following properties:

tensile strength=1.2 N/mm$^2$
elongation at break=744%.

The needles do have the correct length but they are too thick, so no reinforcing effects on the moulded materials are obtained.

What is claimed is:

1. A curable mixture containing
(1) an epoxide resin, and
(2) a curing agent for epoxide resins, wherein (a) at least one of the components (1) and (2) is at least trivalent,
(b) the components (1) and (2) together consist to the extent of at least 60 percent by weight of aliphatic chain segments,
(c) the number of atoms in the chains of components (1) and (2) between two active groups is 25 to 700, a phenylene group being reckoned to have 4 atoms, and
(d) the components (1) and/or (2) contain aliphatic chain segments in the form of polyester or polyether groups, or hydrocarbon radicals unsubstituted or substituted in the side chain; the curable mixture also containing
(2) an amount of 1 to 20 percent by weight, relative to the total amount of components (1) to (2), of needle-shaped to rod-shaped crystals which are insoluble in epoxide resin, and which have a length of 0.1 to 600 μm, a thickness of 0.01 to 60 μm, a length/thickness ratio of 3 to 200, and a density of 1.3 to 3.0.

2. A curable mixture according to claim 1, which contains as component (3) anhydrous, needle-shaped aluminium monohydroxycarboxylic acid salts which are obtained by reaction of neutral or basic aluminium oxide or aluminium hydroxide with acetic acid, propionic acid, benzoic acid, a dicarboxylic acid of the formula $HO_2C-C_nH_{2n}-CO_2H$, wherein n is a number from 3 to 10 inclusive, or with the anhydrides of carboxylic acids, which salts are 0.1 to 200 μm long and 0.01 to 10 μm thick, and have a length/thickness ratio of 5:1 to 50:1.

3. A mixture according to claim 2 wherein the length/thickness ratio of the aluminum salts is 10:1 to 20:1.

4. A curable mixture according to claim 1, wherein at least one of the components (1) and (2) consists to the extent of at least 90 percent by weight of aliphatic chain segments.

5. A curable mixture according to claim 1, wherein the number of atoms in the chains of the components (1) and (2) together is 80 to 350.

6. A curable mixture according to claim 1, which mixture contains 5 to 12 percent by weight of the needle-shaped crystals.

7. A curable mixture according to claim 1, which mixture contains as component (1) a compound having three epoxide groups.

8. A curable mixture according to claim 1, which mixture contains as component (1) triglycidyl isocyanurate.

9. A curable mixture according to claim 1, which mixture contains as component (2) a linear acid polyester or polyether having terminal carboxyl groups.

10. A curable mixture according to claim 1, which mixture contains as component (2) an acid adipic acid neopentyl glycol polyester.

11. A curable mixture according to claim 1, which mixture contains as component (1) a linear polyether or polyester having terminal glycidyl groups bound ether-like or ester-like, the molecular weight being between 1600 and 6000, and as component (2) a polyamine having at least 3 amine hydrogen atoms active in the curing process.

* * * * *

UNITED STATES PATENT AND TRADEMARK OFFICE
CERTIFICATE OF CORRECTION

PATENT NO. : 4,294,745
DATED : October 13, 1981
INVENTOR(S) : Rolf Schmid

It is certified that error appears in the above—identified patent and that said Letters Patent is hereby corrected as shown below:

Claim 6, Column 12, line 12 reads:

"mixture contains 5 to 12 percent by weight of the nee-"

Should read:

-- mixture contains as component (3) 5 to 12 percent by weight of the nee- --

Signed and Sealed this

Sixteenth Day of March 1982

|SEAL|

*Attest:*

*Attesting Officer*

GERALD J. MOSSINGHOFF

*Commissioner of Patents and Trademarks*